United States Patent [19]
Baiel et al.

[11] Patent Number: 5,730,844
[45] Date of Patent: Mar. 24, 1998

[54] LIQUID PHTHALIC ANHYDRIDE RECOVERY PROCESS USING A RECTIFICATION TOWER WITH BENZOIC ACID CONTROL

[75] Inventors: James J. Baiel, Morris Plains, N.J.; Larry O. Jones, Baton Rouge, La.

[73] Assignee: Exxon Chemical Patents Inc., Houston, Tex.

[21] Appl. No.: 758,559

[22] Filed: Nov. 29, 1996

[51] Int. Cl.$^6$ ................................. C07D 307/89
[52] U.S. Cl. ................ 203/56; 203/51; 549/248; 549/249; 549/250
[58] Field of Search ............... 203/51, 56; 549/248, 549/249, 250

[56] References Cited

U.S. PATENT DOCUMENTS

| | | | |
|---|---|---|---|
| 3,178,452 | 4/1965 | Smith et al. | 260/346.4 |
| 3,303,203 | 2/1967 | Melnstein | 260/346.7 |
| 3,380,896 | 4/1968 | Scheiber et al. | 203/77 |
| 3,397,121 | 8/1968 | Fitzgerald | 203/35 |
| 3,507,886 | 4/1970 | Suter et al. | 260/346.7 |
| 3,650,906 | 3/1972 | Gehrken et al. | 203/89 |
| 3,655,521 | 4/1972 | Behrken et al. | 203/28 |
| 3,681,399 | 8/1972 | Barth | 260/346.7 |
| 3,725,211 | 4/1973 | Gehrken et al. | 203/74 |
| 4,285,870 | 8/1981 | Keunecke et al. | 260/346.7 |
| 4,285,871 | 8/1981 | Keunecke et al. | 260/456 |
| 4,568,427 | 2/1986 | Danz et al. | 203/42 |
| 5,214,157 | 5/1993 | Healy et al. | 549/250 |
| 5,508,443 | 4/1996 | Dengler | 542/250 |

FOREIGN PATENT DOCUMENTS 1121645   4/1956   France .......... 14/1

Primary Examiner—Timothy McMahon
Attorney, Agent, or Firm—John F. Hunt

[57] ABSTRACT

A process for recovering phthalic anhydride as a liquid from a vapor phase oxidation product which comprises mixing the vapor phase oxidation product having a temperature of about 130° C. or greater with a first stream comprising maleic anhydride, benzoic acid present in an amount of less than 8 mole %, based on the total concentration of the first stream, and at least one compound selected from the group consisting of: citraconic anhydride and phthalic anhydride, in a rectification tower such that a substantial portion of the phthalic anhydride contained within the vapor phase oxidation product transfers from the vapor phase to a liquid phase and a substantial portion of the by-products contained in the first stream which are more volatile than phthalic anhydride transfer from the liquid phase to the vapor phase and wherein a vapor-to-liquid weight ratio in the range between about 2 to 20 is exhibited within the rectification tower, thereby forming a liquid phase phthalic anhydride product having a phthalic anhydride concentration in the range between about 50–100 wt. %.

21 Claims, 5 Drawing Sheets

LIQUID PHTHALIC ANHYDRIDE RECOVERY PROCESS USING A RECTIFICATION TOWER WITH BENZOIC ACID CONTROL

The present invention generally relates to a method and system for continuously recovering liquid phase phthalic anhydride from a vapor phase oxidation product without the formation of a solid phase. In particular, the present invention improved the overall efficiency of the liquid phase phthalic anhydride recovery process by substantially reducing the benzoic acid concentration in the reflux condenser liquid stream; thereby avoiding freezing thereof. Increased contacting efficiency in the rectification tower by pulsing the reflux to the tower section or recycling of liquid collected from the bottom of each stage in the tower to the top of the stage also increases the efficiency of the liquid phthalic anhydride recovery process. Finally, in the instance where phthalic anhydride is formed from a naphthalene feed, it has been discovered that removal of naphthoquinone from the reflux condenser liquid stream reduces the melting point of the stream; thereby avoiding freezing thereof.

BACKGROUND OF THE INVENTION

Phthalic anhydride is an important commercial chemical useful in the manufacture of plasticizers, polyesters, alkyd resins and dyes.

Phthalic anhydride is typically produced from raw materials such as orthoxylene (o-xylene), petroleum naphthalene, and coal-tar naphthalene. Various well known processes are currently being used in the production of phthalic anhydride, i.e., (1) air oxidation of o-xylene in fixed-bed reactors, (2) air oxidation of petroleum or coal tar naphthalene in fixed-bed reactors, (3) fluid bed oxidation of o-xylene, (4) fluid bed oxidation of petroleum or coal tar naphthalene, and (5) liquid phase oxidation of o-xylene or naphthalene.

U.S. Pat. No. 5,214,157(Healy et al.), which issued on May 25, 1993, is incorporated herein by reference and generally discloses the formation of phthalic anhydride via the vapor phase oxidation of o-xylene. In accordance with the process described in U.S. Pat. No. 5,214,157, o-xylene and air are catalytically converted into a vapor phase oxidation product, i.e., a reaction gas composed of nitrogen, oxygen, water, carbon dioxide, carbon monoxide, phthalic anhydride, maleic anhydride, maleic acid, benzoic acid, o-toluic acid, and partial oxidation products such as phthalide. This vapor phase oxidation product is typically first cooled to generate steam and then delivered to expensive switch condensers, where it is cooled to permit the desublimation of a crude phthalic anhydride stream from the gas. Thereafter, the crude phthalic anhydride is sent to a finishing section in order to produce substantially pure phthalic anhydride.

The switch condensers operate alternatively on cooling and heating cycles in order to first collect the phthalic anhydride as a solid and then melt it for removal from the condensers. The use of switch condensers to separate crude phthalic anhydride from a vapor phase oxidation product is also described in U.S. Pat. No. 5,214,157, which is incorporated herein by reference. Typically, the reactor vapor phase oxidation product is cooled close to the solidification point 131° C.(268° F.) of phthalic anhydride and any condensed liquid is separated out before the remaining vapor enters the switch condensers. The switch condensers desublime the vapor phase oxidation product using the cold condenser oil, and then melt off the solid phase crude phthalic anhydride product using a hot condenser oil heated with steam.

A substantial amount of impurities exit switch condensers as part of the vapor stream, whereas the crude phthalic anhydride product is plated out on the heat exchange tubes as a solid during the cooling step and exits the switch condensers at the bottom as a liquid during the melting step. The vapor gases from the switch condensers are sent to waste gas incinerators where the by-products are destroyed by oxidation to carbon dioxide and water.

Unfortunately, switch condensers contribute to a significant portion of the capital and operating costs of a phthalic anhydride plant. Also, switch condensers operate in a batch mode on 3–6 hours cycles to desublime solid phthalic anhydride on the heat exchange tubes. Another problem associated with switch condensers is that they necessitate frequent maintenance which requires that designated switch condensers be taken out of service on a periodic basis. Maintenance of switch condensers is costly due to the high labor requirement and condenser down time.

A unique process scheme which avoids the need to use expensive switch condensers to recover the phthalic anhydride from the vapor phase oxidation product is disclosed in U.S. patent application, Ser. No. 08/431,647 (Dengler and Baiel), filed on May 2, 1996, which is incorporated herein by reference. This unique process continuously condenses and recovers phthalic anhydride by rectification without the formation of an intermediate solid phase, wherein the more volatile by-products are taken overhead.

The continuous liquid recovery process disclosed in co-pending application, Ser. No. 08/431,647 provides the following advantages over conventional switch condensers: (1) fewer pieces of processing equipment; (2) continuous rather than a batch mode of operation; (3) higher recovery of the phthalic anhydride from the vapor phase oxidation product; (4) an economic advantage which increases with higher concentrations of organics in the vapor phase oxidation product; (5) provides concentrated liquid maleic anhydride, citraconic anhydride and benzoic acid by-product streams which could be upgraded for commercial sale; and (6) benefits the environment since the waste gas contains less by-products and less phthalic anhydride.

Others have attempted to recover liquid phthalic anhydride from the reaction gases of the catalytic oxidation of o-xylene and/or naphthalene without the formation of a solid phase by absorption, wherein the reaction gases are contacted with an organic absorbent (i.e., a mass separating agent) such that the gas is absorbed in the absorbent.

Absorption is described in *Perry's Chemical Engineerings' Handbook* Sixth Edition, McGraw-Hill Book Company, pp. 13-9 and 18-3. Perry describes absorption as "the transfer of a soluble component in a gas-phase mixture into a liquid absorbent whose volatility is low under process conditions".

Absorption processes operate on the theory that by introducing either fresh or recycled mass separating agents or absorbents at the top of the absorption zone the absorbents will contact the upflowing reaction gases, wherein the absorbents are then loaded with the desired product and then removed from the absorbent zone as a liquid bottoms.

Therefore, the bottoms product from a phthalic anhydride absorption process would typically include a substantially large concentration of absorbent, phthalic anhydride, maleic anhydride and other by-products of the catalytic oxidation of o-xylene and/or naphthalene. Thereafter, the bottoms stream itself containing substantial amounts of the desired phthalic anhydride is primarily recycled as additional absorbent and a portion is withdrawn for further processing to recover the maleic anhydride from the crude phthalic anhydride for further recycle.

One conventional absorption method involves the washing out or dissolving of phthalic anhydride and maleic anhydride from a reaction gas stream by contacting the gas stream with either a dibutyl phthlate or dipropyl phthalate absorbent. This method is disadvantageous since the absorbent or mass separating agent must be successively subjected to distillation, crystallization, and purification before it can be returned for further absorption. Moreover, the absorbent contaminates the resulting phthalic anhydride requiring additional downstream separation.

Still others have used tetradecane, petadecane and hydrocarbons primarily consisting of $C_{26}$ to $C_{44}$ paraffins as mass separating agents (i.e. absorbents). These too introduce outside impurities into the crude phthalic anhydride product.

U.S. Pat. No. 4,285,871 (Keunecke et al.), which issued on Aug. 25, 1981, discloses a process for the continuous separation of phthalic anhydride from the reaction gas of the catalytic oxidation of o-xylene and/or naphthalene wherein the reaction gas is treated with a maleic anhydride-based absorbent (i.e., mass separating agent) containing from 0 to 85% by weight phthalic anhydride. Due to the larger pumparound rates required to removed heat from the gas, the material balance of the overall system according to Keunecke '871 suggests that the concentration of phthalic anhydride which exits the absorber vessel is essentially the same as that contained in the maleic anhydride-based absorbent. As such, the phthalic anhydride concentration discharged from the bottom of the absorber vessel is between about 0 to 85 wt. %, based on the total amount of phthalic anhydride contained in the reaction gas. Additionally, a large portion of this liquid phthalic anhydride is continuously being recycled back to the absorption vessel with the large recycle absorbent stream. Recycling of liquid phthalic anhydride back to the absorbent vessel decreases the effectiveness of the method disclosed in the present invention, i.e., separation of phthalic anhydride from the reaction gas.

U.S. Pat. No. 4,285,870 (Keunecke et al.), which issued on Aug. 25, 1981, discloses a process for the continuous separation of phthalic anhydride from the reaction gas of the catalytic oxidation of o-xylene and/or naphthalene which comprises treating the reaction gas in a first absorption stage with an absorbent (i.e., mass separating agent) comprising benzoic acid and phthalic anhydride, and in at least one additional absorption stage with a liquid, maleic anhydride-based absorbent containing from 0 to about 90% by weight phthalic anhydride. The phthalic anhydride concentration discharged from the bottom of the absorber vessel as a liquid according to Keunecke '870 is between about 0 to 90 wt. % (preferably 40–75 wt. %), based on the rates provided in the example. Keunecke '870 also teaches away from the separation process of the present invention since it, like Keunecke '871, recycles liquid phthalic anhydride together with substantial quantities of both a benzoic acid and/or maleic anhydride absorbent.

Because of the recycling of liquid phthalic anhydride with the absorbent, neither Keunecke '870 nor Keunecke '871 are able to attain a high weight percent of phthalic anhydride concentration in the bottoms stream taken from the absorbent vessel as does the rectification method according to the present invention. This is due to the fact that the absorbent process requires the recycling of substantial amounts of a mixture of liquid maleic and phthalic anhydride (i.e., the absorbent) which acts to absorb the upflowing phthalic anhydride and maleic anhydride gases and take them out as bottoms liquids together with the recycled absorbent.

A fundamental disadvantage of the above described absorption processes is they require rather expensive absorbent recovery and recycle systems in order to maintain the maleic anhydride material balance, within acceptable process conditions such that the amount of these by-products leaving the overall phthalic anhydride recovery system is not greater than the amount of these by-products contained in the reaction gas of the catalytic oxidation of o-xylene and/or naphthalene.

In order to maintain the material balance of the by-products of the catalytic oxidation of o-xylene and/or naphthalene, both U.S. Pat. Nos. 4,285,870 and 4,285,871 incorporate expensive and sophisticated maleic anhydride recovery systems. According to both these patents, the gas leaving the absorption zone contains so much maleic anhydride that is necessary to recover the maleic anhydride by scrubbing the gas stream with water or an aqueous maleic acid solution in a scrubbing column at a temperature in the range between 30° C. to 50° C. The water or maleic acid absorbent is fed to the scrubber and enriched there to about 40% by weight. It then passes from the scrubbing column into a thin-layer evaporator, in which the solution is concentrated to about 100% by weight maleic acid. The maleic acid passes from the thin-layer evaporator into a dehydrator wherein the acid is dehydrated into maleic anhydride. A portion of the maleic anhydride is taken overhead from the dehydrator and returned to the second stage of the absorption column to maintain the maleic anhydride material balance. In Keunecke '871, 0.4 kg maleic anhydride per kilogram of recovered phthalic anhydride is scrubbed, dehydrated and returned to the second stage absorption column.

The present inventors have discovered that it is more economical and much more efficient to treat the vapor phase oxidation reaction gases by rectification, whereby a liquid phthalic anhydride product having a phthalic anhydride concentration of between about 50 to 100 wt. %, more preferably 90 to 100 wt. %, is recovered as bottoms and the maleic anhydride and other light by-products are taken out as vapor overhead. Moreover, the separation by rectification also avoids the need to recycle a substantial portion of the phthalic anhydride bottoms stream back into the absorbent zone for the purpose of assisting in the absorption of upflowing gases (except for temperature and concentration control purposes). Recycling of liquid phthalic anhydride is obviously counter-productive in any process which is attempting to purify the phthalic anhydride from its original reaction gases. Also, the rectification tower process permits separation at the higher end of the 50–100 wt. % phthalic anhydride range which significantly reduces the amount of downstream fractionation required to produce a substantially pure phthalic anhydride product of about 99.7 wt. %.

As such, the continuous liquid recovery process of the present invention does not utilize an absorption process to separate a liquid phthalic anhydride product from the reaction gases of the catalytic oxidation of o-xylene and/or naphthalene. Instead, the present inventors have discovered that by contacting a vapor phase oxidation product gas with a by-product(s) stream of the recovery process which has a freezing point which is lower than the freezing point of pure phthalic anhydride in a rectification tower, a crude liquid phase product containing 50 to 100 wt. % phthalic anhydride can be readily separated from a vapor stream having maleic anhydride and other light by-products contained in the gas.

The substantial technical differences between using absorption versus rectification for separating out phthalic anhydride from a vapor phase oxidation gas product without the formation of an intermediate solid phase can be understood by comparing the vapor to liquid weight ratios (V/L) in the absorbent tower against the V/L for the rectification tower. For example, the V/L for the absorbent tower of Keunecke '871, as calculated from the example provided therein is 0.3 to 0.7. The rectification tower of the present invention exhibits a V/L ratio of between 2 to 20, more preferably 8 to 18. That is, due to the substantial pumparound or recycling of the bottoms stream which is required in any absorbent case, its V/L ratio is only a fraction of that which occurs during rectification. The low V/L ratio in the absorbent case of Keunecke '871 clearly demonstrates that due to these high pumparound rates the absorbent tower is not providing any noticeable degree of separation of liquid phthalic anhydride from a vapor phase maleic anhydride, such as that recited in the present invention.

A unique process wherein crude liquid phthalic anhydride having a phthalic anhydride concentration in the range of between 50 to 100 wt. % can be taken as bottoms from a rectification tower, thereby permitting operation at the higher end of the phthalic anhydride concentration range which requires substantially less maleic anhydride recovery from the crude liquid phthalic anhydride then that which is required using an absorbent step as the initial step in treating the vapor phase oxidation product is disclosed in co-pending U.S. patent application, Ser. No. 08/431,647 (Dengler and Baiel), filed on May 2, 1996, which is incorporated herein by reference.

The liquid phthalic anhydride recovery process disclosed in U.S. patent application, Ser. No. 08/431,647 also allows for recovery of phthalic anhydride by controlling the liquid phase compositions and their freezing points by refluxing or recycling a condensed portion of the overhead from the rectifier.

The liquid phthalic anhydride recovery process accomplishes this recovery by partially condensing and refluxing a condensed liquid by-products stream of primarily maleic anhydride, benzoic acid and citraconic anhydride at a temperature sufficient to avoid solidification of the condensate and/or the condensing of a separate water phase. Moreover, the vapor phase oxidation product is cooled directly in the liquid phthalic anhydride recovery process. In Keunecke '870 and '871, the heat is removed indirectly by cooling the recycle absorbent streams. This indirect cooling method has the disadvantage of requiring large liquid pumparound rates.

The present inventors, however, have discovered that the liquid phthalic anhydride recovery process disclosed in U.S. patent application, Ser. No. 08/431,647, under certain conditions, exhibited rectification tower reflux having a temperature above the desired range of 30°–54° C. (87°–130° F.) to avoid freezing thereof.

Early computer modeling of the liquid phthalic anhydride recovery process was done using a theoretical solid-liquid equilibrium model. This model predicted that a reflux mole % mixture of 64% maleic anhydride, 10% citraconic anhydride, 14% benzoic acid and 12% phthalic anhydride would freeze at 25° C. (77° F.). In fact, actual laboratory data and an updated model based on this data show that the reflux taken overhead from the rectification tower will freeze at about 64° C. (148° F.), which is well above the range of 30°–54° C. (87°–130° F.) required to minimize the loss of maleic anhydride and citraconic anhydride.

Through extensive equilibrium modeling and laboratory testing, the present inventors have discovered that benzoic acid concentration is critical to the rectification tower reflux freezing point. That is, benzoic acid has been discovered to be a relatively non-ideal material in the mixture which makes up the condensate from the condenser unit above the rectification tower and the reflux to the rectification tower. This non-ideality causes the freezing point of the condensate to be higher than originally predicted. Thus, the present inventors have discovered that if the benzoic acid concentration of the reflux is kept below about 8 mole %, and more preferably below 6 mole %, acceptable freezing point depressions could be achieved.

By removing the benzoic acid and increasing the relative concentrations of PAN, MAN and CAN, in the reflux the present inventors have discovered that the freezing point thereof can be lowered significantly. Thus, the gas temperature leaving the condenser can be lowered sufficiently to significantly reduce the amounts of PAN, MAN and CAN leaving as vapor in the gas exiting the condenser.

To reduce the benzoic acid concentration, the present inventors have uniquely modified the liquid phthalic anhydride recovery process such that a slipstream of the condensed overhead material is taken and processed by normal distillation. During this distillation maleic anhydride and citraconic anhydride are separated overhead and recycled to the liquid phthalic anhydride rectification tower as reflux. Moreover, the bottoms stream from the rectification tower bypasses the rectification tower reflux and is sent directly to the liquid phthalic anhydride rectification tower bottoms. This new process scheme developed by the present inventors allows the benzoic acid to be controlled to the desired 1–8 mole %, and more preferably 1–6 mole %, level in the liquid phthalic anhydride rectification tower reflux.

The present inventors also recognized that catalysts are known to produce different slates of reaction products. The slate of reaction products will also vary with the feed to the oxidation reaction. For example, naphthalene feed produces naphthoquinone as one by-product not found with o-xylene feed. As with catalysts for o-xylene feed, the product distribution from oxidation of naphthalene can be expected to vary depending on the catalyst and the composition of the feed (e.g., sometimes, coal tar naphthalene is used which is only 95% naphthalene). Therefore, the present inventors have discovered that it is critical to remove naphthoquinone from the by-product stream to substantially reduce its concentration within the rectification tower.

Furthermore, the present inventors have discovered the importance of water in the vapor phase oxidation product to the liquid phase phthalic anhydride recovery process. This water comes from two sources, the humidity in the air feed and the reaction of oxygen with hydrogen in the feed hydrocarbon. Climates vary and the average mount of water in the feed gas will vary with the relative humidity on any given day. The amount of water from the reaction will be constant for a given catalyst over a long period of time, but will vary with catalyst depending on the selectivity properties of the catalyst. Further, the total amount of water will increase with the increase in the concentration of hydrocarbon in the feed gas.

Water is a reactive by-product with respect to the mainly anhydride organic reaction products. In the current commercial phthalic anhydride recovery processes using switch condensers, the temperature of the gas exiting the switch condenser is always greater than the dew point of water to prevent condensation of bulk water with the desublimed phthalic anhydride solid phase and subsequent reaction of anhydride to acid. Even so, there is a significant amount (i.e., a few percent based on PAN) of acid formed by absorption of the gaseous water by the PAN solid phase and subsequent conversion of the anhydride to acid. This acid is subsequently reconverted to anhydride by heating the crude PAN melted from the switch condensers at a sufficiently high temperature (i.e., 250°–280° C.) under a slight vacuum that removes the evolved water.

Similarly, water is present in the vapor phase oxidation product fed to the rectification tower of the present invention. Moreover, the water is taken overhead from the rectification tower as a vapor phase and when cooled by the condenser will absorb into the liquid condensate and react with the anhydrides present to form the corresponding acids which have much higher freezing points than their respective anhydrides. Thus, the formation of any acid in the condensate and reflux to the rectification tower will tend to increase the temperature at which a solid phase begins to form and precipitate from the condensate/reflux.

As these acids are introduced to the rectification tower, they will tend to re-convert to the anhydride and release water. However, this leads to an increase of the concentration of water in the gas exiting the top of the rectification tower because of the mole of water carried with each mole of converted anhydride in the reflux stream. Since the rectification tower is a short residence time device, not all of the acid may be re-converted and some acid may exit the bottom of the tower. Excessive acids and water vapor in the rectification tower can lead to corrosion and plugging on rectification tower internals. Any deposition of solid phthalic acid may lead to formation of dangerous pyrophoric compounds through the corrosive action of the acid on the rectification tower and internals.

The present inventors have also developed a unique method for removing acids from the reflux of the rectification tower overhead and converting them to anhydrides and removing water overhead prior to returning the anhydride to the rectification tower, thereby avoiding the plugging and/or water corrosion problems discussed above.

The liquid phthalic anhydride recovery process disclosed in co-pending U.S. patent application, Ser. No. 08/431,647 (Dengler and Baiel), filed on May 2, 1996, operates near the upper vapor to liquid weight ratio limit for liquid contacting and wetting for such devices (i.e., approximately between about 5–20). This can lead to a poor distribution of liquid on the contacting surfaces causing poor stage efficiency for the process or solids deposition.

The present inventors have discovered a means to improve the liquid distribution and wetting of the rectification tower for the liquid phthalic anhydride recovery process. The improvement can be achieved in two ways: (1) reflux pulsing within the rectification tower; and (2) internal recycle between the bottom and top of each equilibrium tray or stage.

SUMMARY OF THE INVENTION

A process for recovering phthalic anhydride as a liquid from a vapor phase oxidation product which comprises mixing the vapor phase oxidation product having a temperature of about 130° C. or greater with a first stream comprising maleic anhydride, benzoic acid present in an amount of less than 8 mole %, based on the total concentration of the first stream, and at least one compound selected from the group consisting of: citraconic anhydride and phthalic anhydride, in a contacting means such that a substantial portion of the phthalic anhydride contained within the vapor phase oxidation product transfers from the vapor phase to a liquid phase and a substantial portion of the by-products contained in the first stream which are more volatile than phthalic anhydride transfer from the liquid phase to the vapor phase and wherein a vapor-to-liquid weight ratio in the range between about 2 to 20 is exhibited within the contacting means, thereby forming a liquid phase phthalic anhydride product having a phthalic anhydride concentration in the range between about 50–100 wt. %, more preferably 90–100 wt. %, most preferably 95 to 99.8 wt. %. Preferably, the benzoic acid is present in an amount between about 1–6 mole %, based on the total concentration of the first stream.

A preferred embodiment according to the present invention involves a process for recovering phthalic anhydride as a liquid from a vapor phase oxidation product which comprises: (a) cooling the vapor phase oxidation product to a temperature of about 130° C. or greater; and (b) delivering the vapor phase oxidation product to a contacting means which is capable of causing the vapor phase oxidation product to come into contact with at least one by-product stream having a freezing point which is lower than the freezing point of pure phthalic anhydride such that a substantial portion of the phthalic anhydride contained within the vapor phase oxidation product transfers from the vapor phase to a liquid phase and a substantial portion of the by-products contained in the by-product stream which are more volatile than phthalic anhydride transfer from the liquid phase to the vapor phase and wherein a vapor-to-liquid weight ratio in the range between about 2 to 20 is exhibited within the contacting means, provided the by-product stream contains benzoic acid in an amount of less than 8 mole %, based on the total concentration of the by-product stream, thereby forming a liquid phase phthalic anhydride product having a phthalic anhydride concentration in the range between about 50 to 100 wt. %, and a first vapor stream; the contacting means is also capable of separating the liquid phase phthalic anhydride product from the first vapor stream.

Preferably, steps (a) and (b) immediately above can be followed by steps: (c) removing the liquid phase phthalic anhydride product from the contacting means as bottoms; (d) removing the first vapor stream from the contacting means as overhead; (e) cooling the first vapor stream to a temperature in the range between about 25° C. to 80° C., thereby forming a first by-product stream and a second vapor stream; (f) separating the first by-product stream from the second vapor stream; and (g) recycling at least a portion of the first by-product stream to the upper section of the contacting means.

Optionally, steps (a) and (b) above can be followed by steps: (c) cooling the first vapor stream to a temperature in the range between about 25° C. to 80° C. in the upper section of the contacting means, thereby forming a first by-product stream and a second vapor stream; (d) separating the first by-product stream from the second vapor stream in the upper section; (e) transferring the first by-product stream to the top of the contacting means; (f) removing the liquid phase phthalic anhydride product from the contacting means as bottoms; and (g) removing the second vapor stream from the contacting means as overhead.

Additionally, the preferred process may include the following steps: removing at least a portion of the first by-product stream of step (d) from the contacting means, wherein the first by-product stream comprises at least one acid selected from the group consisting of: phthalic acid, maleic acid and citraconic acid; subjecting the first by-product stream which is removed from the contacting means to sufficient heat and pressure to convert any of the acids into their respective anhydrides, thereby forming a dehydrated first by-product stream; and recycling the dehydrated first by-product stream containing the converted acids to the contact means.

Alternatively, the following steps may be used: removing at least a portion of the first by-product stream of step (d) from the contacting means, wherein the first by-product stream comprises at least one acid selected from the group consisting of: phthalic acid, maleic acid and citraconic acid; flashing the first by-product stream which is removed from the contacting means to convert any of the acids into their respective anhydrides, thereby forming a dehydrated first by-product stream; and recycling the dehydrated first by-product stream containing the converted acids to the contact means.

Pulsing of the first by-product stream which is recycled to the upper section of the contacting means can be used to increase wetting of the contacting means. In place of pulsing, another embodiment according to the present invention involves the steps of: removing a liquid mixture comprising the by-product stream and the liquid phase phthalic anhydride product from below at least one of the equilibrium stages; and recycling the liquid mixture to a top portion of the equilibrium stage; whereby the liquid to vapor ratio is increased.

Another preferred embodiment according to the present invention is a process for recovering phthalic anhydride as a liquid from a vapor phase oxidation product generated from the vapor phase oxidation of naphthalene which comprises: (a) cooling the vapor phase oxidation product to a temperature of about 130° C. or greater; and (b) delivering the vapor phase oxidation product to a contacting means which comprises a upper section, an intermediate section and a lower section, the contacting means being capable of causing the vapor phase oxidation product to come into contact with at least one by-product stream having a freezing point which is lower than the freezing point of pure phthalic anhydride such that a substantial portion of the phthalic anhydride contained within the vapor phase oxidation product transfers from the vapor phase to a liquid phase and a substantial portion of the by-products contained in the by-product stream which are more volatile than phthalic anhydride transfer from the liquid phase to the vapor phase and wherein a vapor-to-liquid weight ratio in the range between about 2 to 20 is exhibited within the contacting means, provided the by-product stream contains benzoic acid in an amount of less than 8 mole %, based on the total concentration of the by-product stream, thereby forming a liquid phase phthalic anhydride product having a phthalic anhydride concentration in the range between about 50 to 100 wt. %, and a first vapor stream; the contacting means is also capable of separating the liquid phase phthalic anhydride product from the first vapor stream; (c) cooling the first vapor stream to a temperature in the range between about 25° C. to 80° C. in the upper section of the contacting means, thereby forming a first by-product stream and a second vapor stream; (d) separating the first by-product stream from the second vapor stream in the upper section; (e) refluxing the first by-product stream to the intermediate section of the contacting means; (f) removing the liquid phase phthalic anhydride product from the contacting means as bottoms; (g) removing the second vapor stream from the contacting means as overhead; and (h) diverting at least a portion of the first by-product stream to a separation tower which is capable of separating a third vapor phase from a naphthoquinone-enriched stream. Subsequently returning the third vapor phase and the bottom stream from the separation tower to the top section of the contacting means. Optionally, this process may also comprise the steps of: (i) separating the liquid phase phthalic anhydride product of step (f) into a naphthoquinone-enriched vapor stream and a crude phthalic anhydride stream; and (j) converting any phthalic acid contained within the crude phthalic anhydride stream into phthalic anhydride and any naphthoquinone into heavies. According to this process the crude phthalic anhydride stream contains less than 1 ppm naphthoquinone.

The process for separating phthalic anhydride from a vapor phase oxidation product may also include a by-product (e.g., maleic anhydride) recovery step which includes the following steps: mixing the second vapor stream with an absorbent to form an absorbent containing by-product stream; separating the absorbent containing by-product stream into a desorbed by-product stream and a concentrated absorbent stream; and mixing the desorbed by-product stream with a by-product stream. Alternatively, a maleic anhydride recovery process such as water scrubbing can also be used. One such water scrubbing process is described in Keunecke '870 and '871, which are incorporated herein by reference.

This process for separating an anhydride product in a rectification tower having a vapor-to-liquid weight ratio in the rectification tower between about 2 to 20 and a phthalic anhydride bottoms concentration in the range between about 50 to 100 wt. % from a vapor phase oxidation product by mixing and cooling the vapor phase oxidation product with recycled by-products which have freezing points lower than the freezing point of pure anhydride is also applicable for recovery of crude products other than phthalic anhydride such as maleic anhydride, trimellitic anhydride, benzoic acid and pyromellitic dianhydride.

DESCRIPTION OF THE PREFERRED EMBODIMENTS

A continuous process for recovering phthalic anhydride (PAN) in a liquid phase from a vapor phase oxidation product of o-xylene, naphthalene or the like, and compressed air is hereafter described.

The freezing point of pure phthalic anhydride is 131° C. (268° F.). Conventional switch condensers operate by cooling the vapor phase oxidation product below this temperature to plate out solid phase phthalic anhydride on the heat exchange tubes within each switch condenser.

According to the present invention, the formation of crude liquid phthalic anhydride product without the presence of an intermediate solid phase phthalic anhydride is accomplished by contacting the vapor phase oxidation product with recycled by-products which have lower freezing points than pure phthalic anhydride, whereby the operating temperatures are always above the freezing point of the liquid phase. The present inventors have discovered that in order to maintain an acceptably low freezing point of the recycled by-product stream it is necessary to maintain the level of benzoic acid at less than 8 mole %, preferably 1–6 mole %. An acceptably low freezing point temperature is one that is lower than the temperature of the stream itself and can be designated the stream temperature. It is also desirable to convert any maleic acid, phthalic acid and/or citraconic acid present in the refluxed by-product stream to their respective anhydrides to also assist in keeping the freezing point of the by-product stream acceptably low. It is preferable that the contacting occur in a rectification tower so that a vapor-to-liquid weight ratio within the contacting tower is maintained in the range between about 2 to 20, more preferably 8 to 18.

Figure 1:
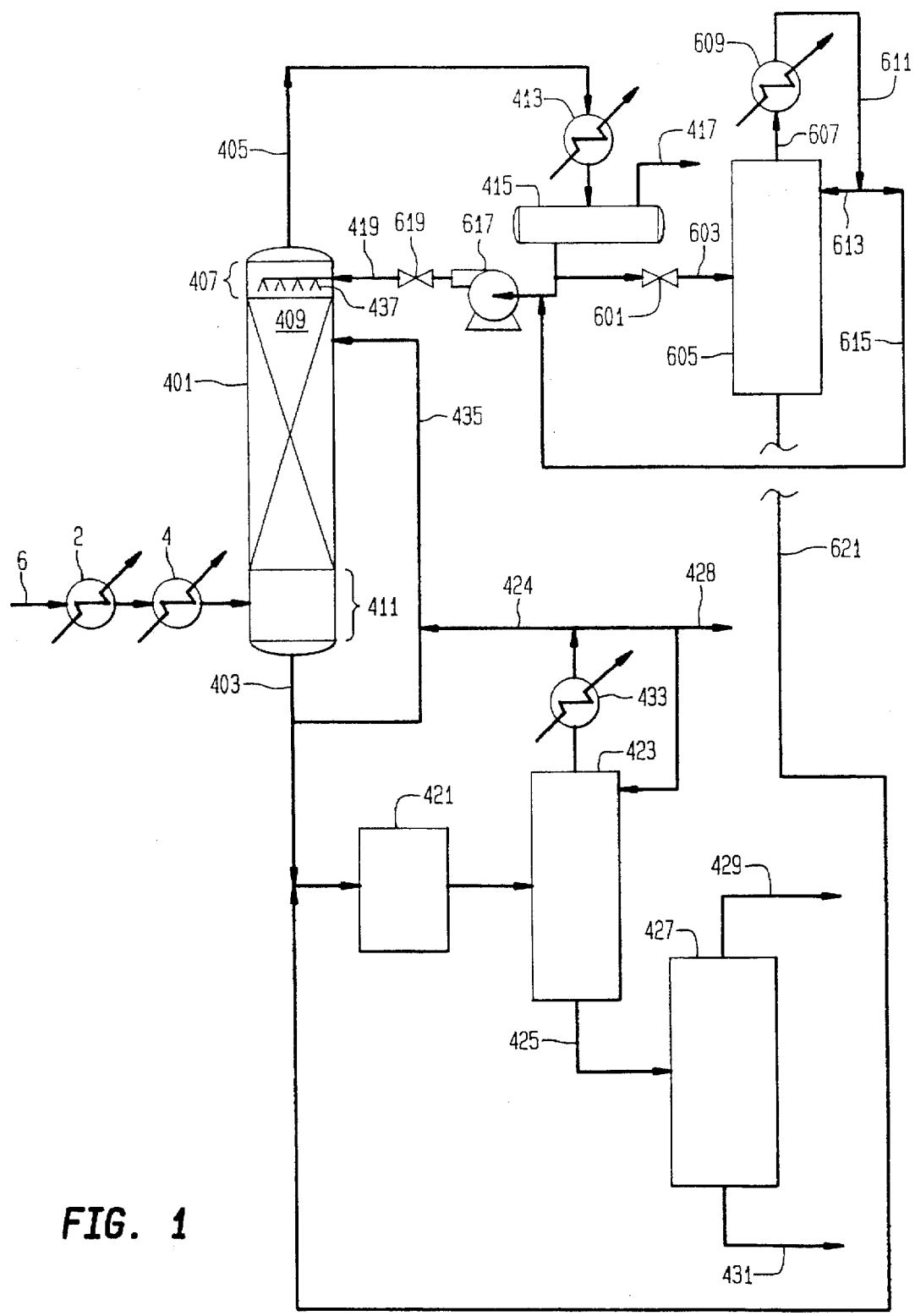
FIG. 1 is a schematic diagram of the phthalic anhydride recovery process in accordance with the preferred embodiment of the present invention wherein a low pressure gas/liquid contactor rectification tower is used in conjunction with external cooling and separating devices, and a benzoic acid recovery step for recycling refluxed by-products back to the rectification tower having a benzoic acid concentration of less than 8 mole %.
Figure 3:
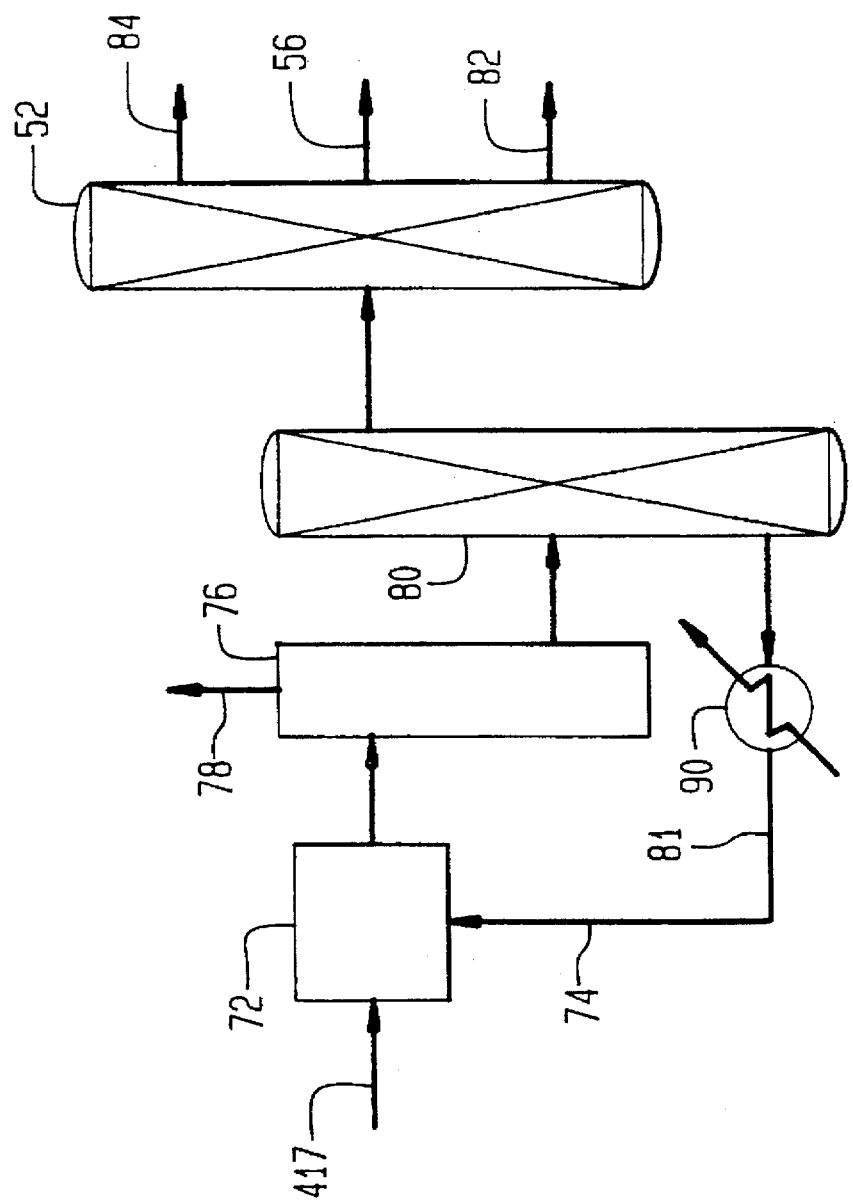
FIG. 3 is a schematic representation of a maleic anhydride recovery system which can be attached to receive the cooled and separated vapor overhead from the processing scheme shown in either FIG. 1 or 2.

The preferred embodiment according to the present invention involves the configuration depicted in FIG. 1. This figure pertains to the use of a contacting or packed tower having an external cooling/condensing system having a means for removing benzoic acid from the condensing system's reflux, whereby the reflux by-products comprise benzoic acid in an amount of less than 8 mole %. FIG. 3 depicts the unique process that can be used to recover maleic anhydride from the vapor phase overhead taken from the process described in FIG. 1.

FIG. 1 describes a process for recovering phthalic anhydride as a liquid from a vapor phase oxidation product. The vapor phase oxidation product of o-xylene, naphthalene, and/or any other material capable of being catalytically converted to phthalic anhydride is passed via conduit 6 through heat exchangers 2 and 4 wherein the vapor phase oxidation product is cooled to a temperature of about 130° C. (266° F.) or greater, preferable in the range between about 130° C. to 177° C. Temperatures higher than 130° C. are less desirable because the additional heat is rejected to cooling water and greater rectifier condenser surface area is required. The cooled vapor phase oxidation product is delivered from conduit 6, following cooling to a temperature no lower than about 130° C., to rectifier or contacting means 401 which is capable of causing the vapor phase oxidation product to come into contact with at least one by-product stream having a freezing point which is lower than the freezing point of pure phthalic anhydride and so that a vapor-to-liquid weight ratio in the range between about 2 to 20 is maintained, thereby forming a liquid phase phthalic anhydride product having a phthalic anhydride concentration of between about 50–100 wt. %, preferably between about 85–100 wt. %, more preferably about 90–100 wt. %, and most preferably between about 95–99.8 wt. %, and a first vapor stream. Rectifier tower 401 separates the liquid phase phthalic anhydride product from the first vapor stream by means of multiple equilibrium stages, i.e., packing or trays, (not shown) disposed therein. Rectifier tower 401 is typically a low pressure drop counter-current gas/liquid contactor having at least 2 low pressure drop equilibrium stages, preferably 3 to 10.

It should be kept in mind that despite operating below the freezing point of phthalic anhydride there is no formation of a solid phase anywhere within rectifier tower 401 due to the choice of operating conditions.

The liquid phase phthalic anhydride product is removed from rectifier tower 401 as bottoms via conduit 403, while the first vapor stream is removed from rectifier tower 401 as overhead via conduit 405. Rectifier tower 401 has an upper section 407, an intermediate section 409 and a lower section 411.

The first vapor stream which is taken as overhead from rectifier tower 401 has a temperature in the range between about 115° to 135° C. (239°–275° F.) at a pressure in the range between about 0.10 to 0.14 MPa (14.7–20 psia).

The first vapor stream taken overhead via conduit 405 is passed through a heat exchanger or low pressure drop gas cooler 413 where it is cooled to a temperature in the range between about 25° C. to 80° C. (77°–176° F.), thereby forming a first by-product stream and a second vapor stream. This mixed phase stream is then delivered to a vapor/liquid disengaging drum 415 (with or without a de-entrainment screen) wherein the first by-product stream is separated from the second vapor stream. The second vapor stream is then taken out overhead via conduit 417 for either maleic recovery (for sales) according to FIG. 3 or disposal via incineration. At least a portion of the first by-product stream is taken out as bottoms from drum 415 via conduit 419 and recycled as reflux to upper section 407 of rectifier tower 401.

This first by-product stream preferably contains about 40 to 95 mole % maleic anhydride, about 0 to 20 mole % citraconic anhydride, about 0 to 50 mole % phthalic anhydride, and about 0 to 35 mole % benzoic acid. It is preferable to divert at least a portion of the first by-product stream traversing through conduit 419 by means of valve 601 and conduit 603 to a distillation or fractionation tower 605 to control the benzoic acid concentration of the first by-product stream to 8 mole % or lower. Otherwise, the mixture disposed in condenser 413 may have a freezing point which is greater than its actual stream temperature, thereby causing the formation of solids therein.

When the first by-product is diverted to fractionation tower 605 light-ends such as maleic anhydride and citraconic anhydride are taken overhead via conduit 607, cooled via heat exchanger 609, and recycled to tower 605 via conduits 611 and 613 and returned to rectification tower 401 via conduits 611,615 and 419. Benzoic acid and phthalic anhydride are recovered as bottoms from fractionation tower 605 and sent to decomposer 421 via conduits 621 and 403.

In the process described in FIG. 1, the liquid/gas rates may be very low so that rectification tower 401 is operating at the limit for liquid contacting and wetting. Loss of liquid wetting and contacting leads to loss of efficiency of rectification tower 401 and possible plugging. In order to increase the contacting efficiency and the liquid wetting in rectification tower 401 it is preferable to pulse the reflux from conduit 419 into the rectification tower 401 via pump 617 and solenoid valve 619. By this technique, the equilibrium stages (not shown) contained within rectification tower 401 are completely and efficiently wetted with the liquid for contacting with the vapor phase oxidation product. After the pulse, the liquid phase phthalic anhydride product will gradually drain from the equilibrium stages. Before the equilibrium stages become dry, another pulse of a refluxed by-product stream follows. No disadvantage, or minimum loss of staging occurs when the pulse frequency is faster than the time constant for draining of the liquid phase phthalic anhydride product. Also, there will tend to be a liquid film that adheres to the equilibrium stages. The pulsed reflux merely refreshes the liquid before it can significantly change from the equilibrium composition.

Figure 4:
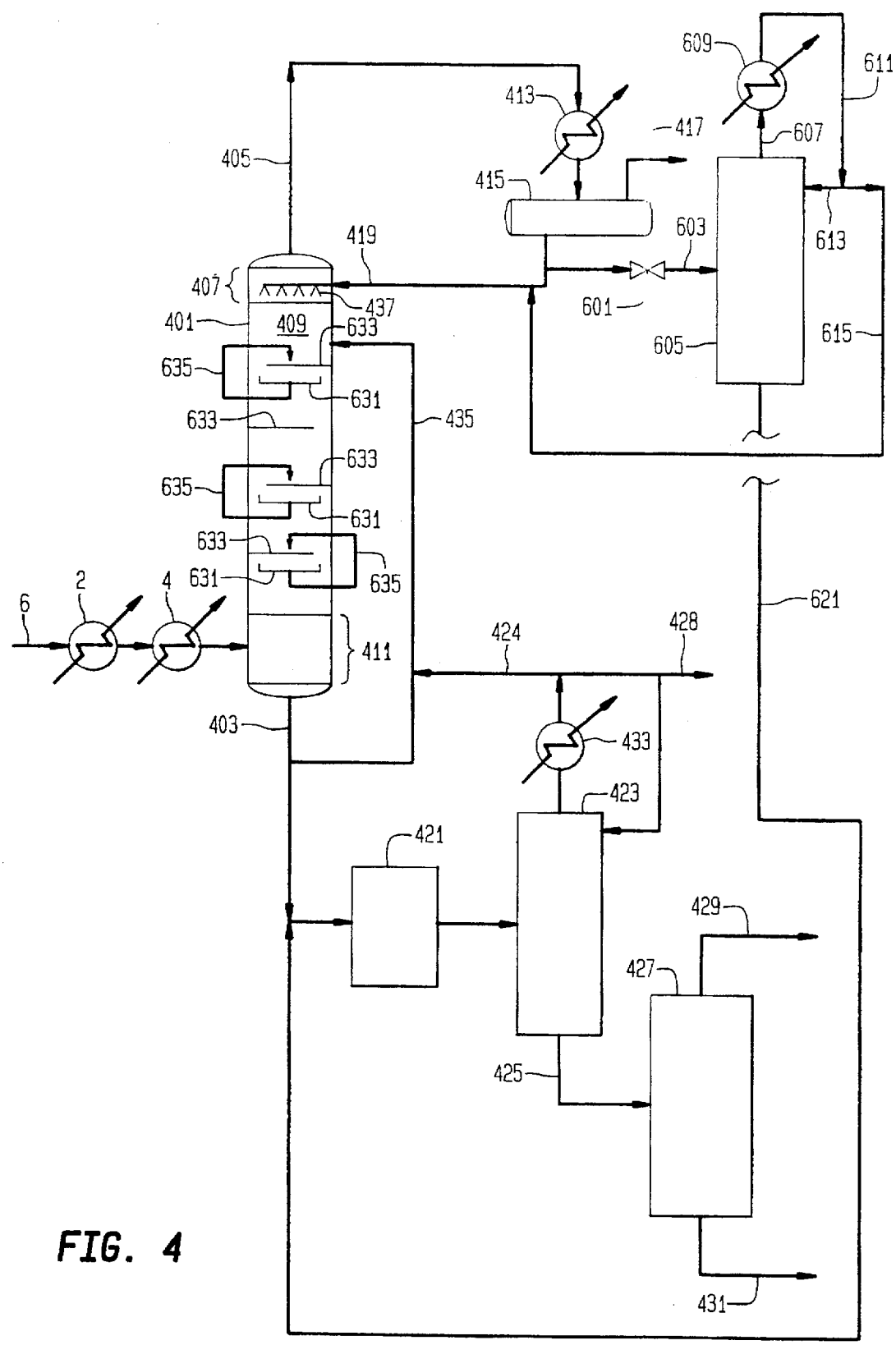
FIG. 4 is the phthalic anhydride recovery system depicted in FIG. 1 wherein individual equilibrium stage recycle means are provided in the rectification tower to increased contacting efficiency.

Alternatively, liquid contacting and wetting of the equilibrium stages of rectification tower 401 can be accomplished by liquid collection from the bottom of a stage and recycling to the top of the stage. This embodiment is clearly depicted in FIG. 4, wherein liquid phase phthalic anhydride product is collected in a liquid re-distributor 631 disposed below each equilibrium stage 633. A portion of the liquid phase phthalic anhydride product is withdrawn and recycled via conduit 635 to the top of the respective equilibrium stage 633 and used to irrigate stage 633.

The advantage of using the pulsed reflux or re-distributor recycle embodiments with the rectification tower is that the liquid ratio can be increased as desired to effect the required amount of liquid to obtain the proper wetting for efficient gas/liquid contacting or to obtain the required liquid ratio to keep all the packing wet with liquid.

The liquid phase phthalic anhydride product which is removed from the rectification tower as bottoms preferably has a concentration of between about 50–100 wt. %, more preferably between about 90–100 wt. %, and most preferably between about 95–99.8 wt. %, phthalic anhydride.

The liquid phase phthalic anhydride product passes via conduit 403, optionally, into at least one decomposer 421 which operates under a slight vacuum (about 700 mm Hg absolute) and high temperatures (e.g., 260° C. (500° F.) to convert the small amount of phthalic acid that is present to phthalic anhydride. Thereafter, the liquid phase phthalic anhydride product is pumped from decomposer 421 to a light ends column or fractionation column 423 wherein a second by-product stream comprising low-boiling by-products, e.g., maleic anhydride, citraconic anhydride and benzoic acid, along with a small amount of phthalic anhydride are removed at the top of fractionation column 423, cooled via heat exchanger 433, and at least a part of this stream is optionally returned to rectifier tower 401 as a second by-product stream via conduits 424 and 435 with the remainder of the stream being purged via conduit 428 from the system to remove benzoic acid. Crude phthalic anhydride is taken as bottoms from fractionation column 423 and is optionally fed via conduit 425 to a second fractionation column 427 wherein substantially pure phthalic anhydride is removed from the top of fractionation column 427 via conduit 429, while heavy products are removed from the bottom via conduit 431.

Optionally, a portion (i.e., 0–50%) of the liquid phase phthalic anhydride product removed as bottoms from rectifier tower 401 via conduit 403 is recycled via conduit 435 to rectifier tower 401 for temperature and concentration control in the tower.

Figure 2:
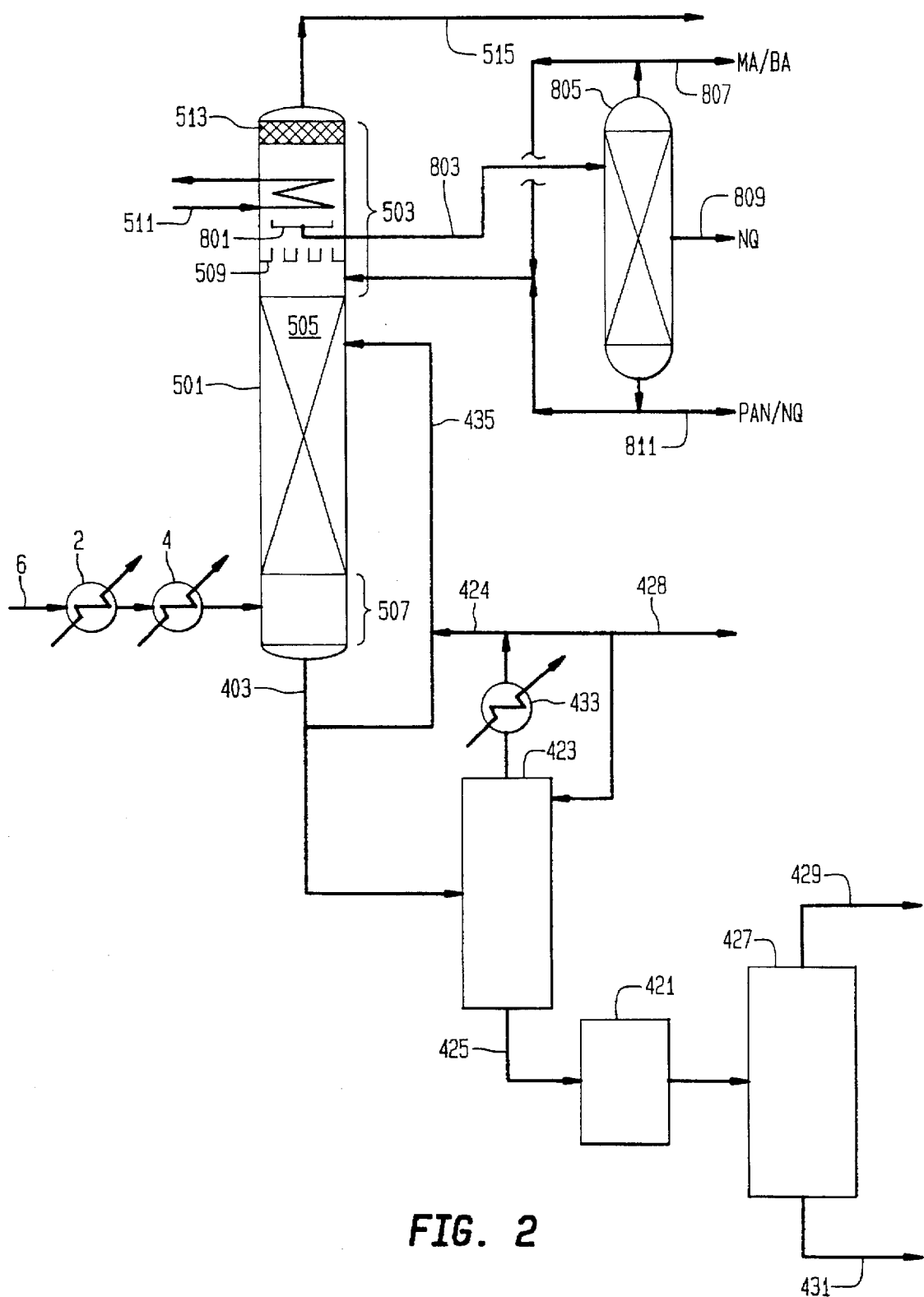
FIG. 2 is a schematic diagram of the phthalic anhydride recovery process in accordance with another embodiment of the present invention wherein an integrated contactor/condenser rectification tower includes an internal reflux section for recycling refluxed by-products back to the rectification section and external naphthoquinone recovery steps which produce a crude phthalic anhydride product having less than 1 ppm naphthoquinone.

FIG. 2 depicts an integrated rectifier tower/cooler condenser unit 501 which may be used in place of rectifier tower 401, cooler 413 and separator 415 of FIG. 1. Integrated unit 501 comprises a upper section 503, an intermediate section 505 and lower section 507.

Liquid phase oxidation product is carried via conduit 6 through heat exchangers 2 and 4 where it is cooled to a temperature no lower than about 130° C. before being sent to lower section 507 of integrated rectifier unit 501. Intermediate section 505 of integrated rectifier unit 501 comprises a low pressure drop gas/liquid contactor having at least 2, preferably 3 to 10 equilibrium stages. Upflowing cooled vapor phase oxidation product contacts a downflowing recycled by-product stream from upper section 503 as it passes through intermediate section 505 causing liquid phase phthalic anhydride to return to lower section 507 while a first vapor phase stream passes through liquid redistributor 509 into upper section 503. While in upper section 503, the first vapor stream is cooled via cooling coils 511 to a temperature in the range between about 25° C. to 80° C., thereby forming a first by-product stream and a second vapor stream. The first by-product stream is returned or recycled to the liquid redistributor and thereafter flows downwardly into intermediate section 505 so as to come into contact with upflowing vapor phase oxidation product, as discussed above. The second vapor stream passes through a vapor/liquid disengaging section disposed at the top of upper section 503. The disengaging section may optionally include a de-entrainment screen 513 wherein any residual liquid phase first by-product stream is separated from the second vapor stream before the second vapor stream is taken overhead via conduit 515 for either maleic recovery (for sales) as shown in FIG. 3 and/or incineration.

The liquid phase containing phthalic anhydride passes through integrated rectifier unit 501 in a downward direction until it reaches lower section 507 where it is removed from integrated rectifier unit 501 as bottoms via conduit 403. The liquid phase phthalic anhydride product is then finished in decomposer 421, fractionation tower 423 and fractionation tower 427 as described above.

Alternatively as shown in FIG. 2, when the liquid phthalic anhydride recovery process is used to recover phthalic anhydride from a vapor phase phthalic anhydride product generated from naphthalene, the by-product naphthoquinone must be removed to less than 1 ppm in the product phthalic anhydride to meet product specifications. However, the by-product naphthoquinone is a valuable commercial product.

Because naphthoquinone is difficult to remove from phthalic anhydride to less than 1 ppm by distillation, the reduction is currently accomplished by heat treating the undistilled phthalic anhydride for long periods at high temperature in a series of decomposers. The naphthoquinone reacts with other compounds to form heavies which are then removed in the bottom of the second finishing section distillation tower during phthalic anhydride purification. A catalyst, such as $NaHCO_3$ or $SnCl_2 \square H_2O$, is required and the reaction is first order in naphthoquinone. The decomposer treatment requires more catalyst, longer time and higher temperature than the corresponding o-xylene feed based processes.

Naphthalene feed brings several new issues to the liquid phthalic anhydride recovery process. First, the distribution of by-products is markedly different. The amount of maleic anhydride and benzoic acid produced appears to be less and there are significant amounts of naphthoquinone. As with benzoic acid in the o-xylene based liquid phthalic anhydride recovery process, the recovery of naphthoquinone will be significantly higher than that obtained with the current switch condenser based processes. Thus, any liquid phthalic anhydride recovery process using naphthalene as feed will be required to handle significantly higher concentrations of naphthoquinone in phthalic anhydride than the current commercial processes.

Almost all of the naphthoquinone produced in accordance with the process depicted in FIG. 2 will be captured by rectification tower 501. Thus, there will be significant concentrations in both the liquid reflux to the section 505 of tower 501 and in the bottoms of tower 501 exiting with the liquid phase phthalic anhydride product.

If present in significant concentrations, the naphthoquinone will almost certainly increase the melting point of the tower reflux. Since the melting point of naphthoquinone is much higher than maleic anhydride a separation removal step for naphthoquinone in the tower reflux may be required. FIG. 2 depicts one possible alternative for recovery naphthoquinone from the tower reflux, wherein a re-distributor 801 removes at least a portion of liquid reflux comprising naphthoquinone which is then carried via conduit 803 to fractionation or distillation tower 805. Distillation tower 805 separates the naphthoquinone reflux liquid taken from tower 501 into an overhead stream 807 (i.e., light-ends comprising mostly of benzoic acid and maleic anhydride), a side stream 809 (i.e., naphthoquinone rich cut) and a bottoms stream 811 (i.e., phthalic anhydride and naphthoquinone depleted bottoms). Streams 807 and 811 are returned to the upper section of tower 501.

Alternatively, naphthoquinone may be removed from the rectification tower reflux by either (1) operating the rectification tower at higher temperatures to overcome the higher melting point of the reflux with the addition of a recovery step to recover maleic anhydride and naphthoquinone in the vapor stream, or (2) operating the rectification tower with an enriched naphthoquinone overhead/reflux stream (and at higher temperatures than the liquid phthalic anhydride process described in FIG. 1 above) which allows balancing the maleic anhydride and naphthoquinone production with that exiting in the vapor.

It is necessary to produce phthalic anhydride product having less than 1 ppm naphthoquinone. If the concentrations of naphthoquinone are higher in the bottoms from rectification tower 501, than currently obtained from the crude PAN melted from switch condensers in conventional processing, the level may need to be reduced before heat treating the crude PAN to react residual naphthoquinone into a heavies fraction removable by distillation.

One alternative is to take the bottoms from tower 501 and pass them via conduit 403 directly to distillation tower 423, concentrate the naphthoquinone in the overhead from tower 423 and reduce the naphthoquinone in the bottoms to less than or equal to the concentration of naphthoquinone in crude phthalic anhydride in the current naphthalene based processes using switch condensers. Thereafter, the bottoms from tower 423 can be processed in decomposer 421 as is crude phthalic anhydride and then fed directly to phthalic anhydride recovery distillation tower 427 and separated as discussed above with regard to FIG. 1.

Overall recovery of the phthalic anhydride from the reactor effluent gas (i.e., vapor phase oxidation product) is approximately 99.7% for both processes described in FIGS. 1 and 2.

Optionally, maleic anhydride in the second vapor phase stream may be recovered in accordance with the unique maleic anhydride recovery process depicted in FIG. 3, wherein the second vapor phase stream is passed via conduit 417 to mixing vessel 72 where it is contacted with dihexylphthalate, or any other ester having a similar boiling point. The ester absorbs approximately 70% of the maleic anhydride which is present in the vapor phase. The maleic anhydride/ester mixture from vessel 72 is then passed to a flash unit 76. The residual vapor is separated and sent via conduit 78 to an incinerator (not shown). The liquid from flash unit 76 containing the absorbed maleic anhydride is separated from the ester via distillation in fractionation column or tower 80. This minimizes the amount of ester in the overhead maleic anhydride stream and especially in recycle stream 56. Virtually all of the ester remaining in the recovered maleic anhydride is removed via purge stream 82. Ester in recycle stream 56 would be purged as a heavy along with the phthalic anhydride residue, unchanged, but would increase the quantity of residue for disposal. The desorbed ester is cooled in heat exchanger 90, and recycled to mixing vessel 72 via conduit 74.

The maleic anhydride recovered from the absorption step in fractionation column 80 is sent to fractionation column 52 optionally along with overhead stream 428 from fractionation column 423. Fractionation column 52 has three product streams, i.e., bottoms, overhead and a recycle side stream. The bottoms are taken out via conduit 82 and primarily include benzoic acid and any heavier components not rejected from fractionation column 50. Unlike other recovery systems, essentially all of the benzoic acid in the reactor effluent gas may be recovered and concentrated in purge stream 82. By adjusting the amount of benzoic acid purged, the benzoic acid content in recycle stream 56 and 424 can be controlled to optimum levels. Although not identified, trace components in this bottoms stream have been shown to cause color problems if not removed from the final purge stream. Essentially all of the ester that goes overhead in column 80 is rejected to this purge stream. The side stream 56 is an impure maleic anhydride recycle stream (i.e., a by-product stream) which contains no significant amounts of phthalic anhydride. Overhead 84 is a higher purity maleic anhydride stream suitable for upgrading for commercial sale.

The side stream of column 52 is preferably recycled via line 56 to the top section of column 401 and/or maleic anhydride can, optionally, be recovered for sales and/or further purification.

The maleic anhydride recovery process described above is unique since only a portion of the maleic anhydride is recovered requiring only one contacting stage compared to multiple stages in other absorption processes. This process also takes advantage of the fact that the phthalic anhydride and other heavies (i.e., trimellitic anhydride and phthalide) are extremely low and thus do not build-up in the absorber circuit, thereby minimizing absorbent purge and make-up.

Instead of esters, an alcohol such as hexyl alcohol or isopropyl alcohol could be used as make-up to the maleic anhydride recovery section. An alcohol which is capable of forming the monoester in-situ from maleic or phthalic anhydride and eventually forming the diester with similar adsorption properties to dihexyl phthalate would be a satisfactory substitute for the esters in the absorption of maleic anhydride.

Figure 5:
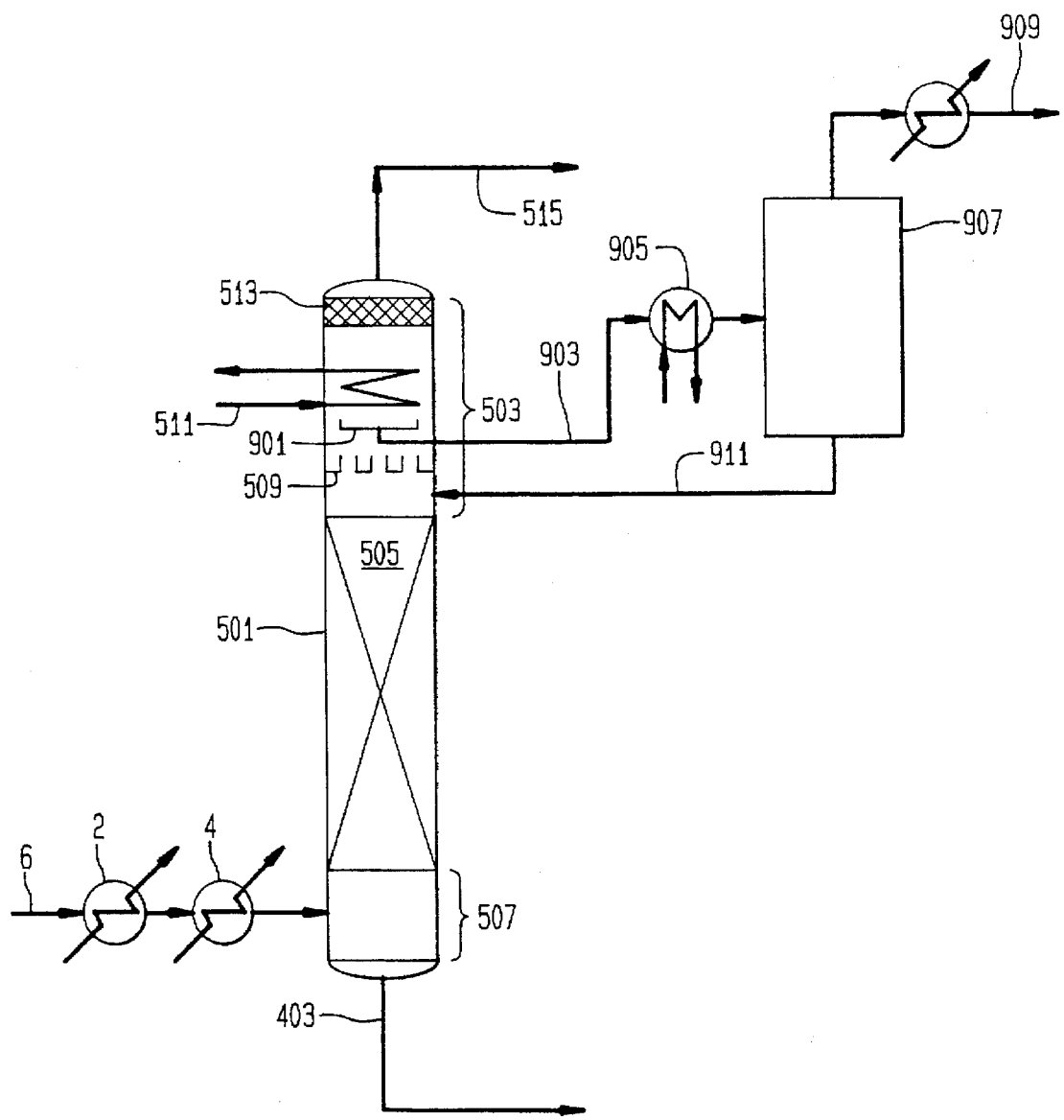
FIG. 5 is a schematic diagram of the phthalic anhydride recovery process in accordance with another embodiment of the present invention wherein an integrated contactor/condenser rectification tower having an internal reflux section for recycling refluxed by-products back to the rectification section also includes a means for converting acids contained within the refluxed by-products to anhydrides.

FIG. 5 is directed to an additional embodiment wherein organic acids are formed in the condenser of rectification tower 501. Note that the configuration of the tower and condenser can be either as in FIG. 1 or as in FIG. 5. Most of the acid formed will be maleic acid with smaller amounts of phthalic acid. Acid formation will tend to raise the melting point of the condensing mixture by replacing lower melting point maleic anhydride with higher melting point maleic acid.

As the liquid reflux works its way toward the bottom of tower 501, the temperature increases and the acids will tend to re-convert to anhydride. However, the acid content may become high enough to cause precipitation and plugging in the condenser and upper regions of tower 501.

FIG. 5 depicts two methods capable of removing acids from the liquid reflux to tower 501 in cases where excess acid contributes to solids formation and plugging in the condenser or in the equilibrium stages of the tower. Vessel 907, where acid formed in the condenser is re-converted to anhydride and the water is removed, can be either a reactor or a single stage flash drum. The reactor or flash drum can be operated at either below, equal to or above atmospheric pressure depending on the temperature achieved by heater 905. A reasonable operating temperature range is 250°–350° C.

FIG. 5 provides a re-distributor 901 which captures and withdraws at least a portion of the reflux stream via conduit 903. In the case where vessel 907 is a reactor, this withdrawn stream is then heated by heater 905 and then held in reactor 907 for 15 minutes to 1 hour to convert any acids therein to anhydrides. Water vapor is removed overhead via conduit 909 and the anhydrides, mostly maleic and phthalic, are returned to rectification tower 501 via conduit 911. Under conditions where the acids are easily converted to anhydrides and the water is easily removed, vessel 907 may be a flash drum with a nominal residence time, typically less than 20 minutes.

This unique process may also be extended to recover other anhydrides and acids such as maleic anhydride, trimellitic anhydride, pyromellitic anhydride, benzoic acid etc. from vapor phase oxidation products without the formation of a solid phase intermediate.

EXAMPLE 1

Table 1 below demonstrates the unexpected effect that benzoic acid concentration has on the liquid mixture freezing points of various reflux compositions.

TABLE 1

| Sample | PAN (moles) | BA (moles) | MAN (moles) | CAN (moles) | Mole % BA | Freezing Point (°C.) |
| --- | --- | --- | --- | --- | --- | --- |
| 1 | 1.0 | 1.4 | 4.9 | 0.7 | 17.5 | 65 |
| 2 | 1.0 | 0.5 | 6.1 | 0.8 | 6.0 | 34 |
| 3 | 1.0 | 0.5 | 6.1 | 1.3 | 5.6 | 32 |

As demonstrated above, a reduction in benzoic acid (as shown in samples 2 and 3) significantly lowers the freezing point of the mixture versus the higher benzoic acid case set forth in sample 1.

What is claimed is:

1. A process for recovering phthalic anhydride as a liquid from a vapor phase oxidation product which comprises mixing said vapor phase oxidation product having a temperature of about 130° C. or greater with a first stream comprising benzoic acid present in an amount of less than 8 mole %, based on the total concentration of said first stream, in a contacting means such that a substantial portion of the phthalic anhydride contained within said vapor phase oxidation product transfers from the vapor phase to a liquid phase and a substantial portion of the by-products contained in said first stream which are more volatile than phthalic anhydride transfer from the liquid phase to the vapor phase and wherein a vapor-to-liquid weight ratio in the range between about 2 to 20 is exhibited within said contacting means, thereby forming a liquid phase phthalic anhydride product having a phthalic anhydride concentration in the range between about 50–100 wt. %.

2. The process according to claim 1 wherein said first stream further comprises maleic anhydride, and at least one compound selected from the group consisting of: citraconic anhydride and phthalic anhydride.

3. The process according to claim 1 wherein said liquid phase phthalic anhydride product concentration is in the range between about 90 to 100 wt. %.

4. The process according to claim 1 wherein said benzoic acid is present in an amount between about 1–6 mole %, based on the total concentration of said first stream.

5. A process for recovering phthalic anhydride as a liquid from a vapor phase oxidation product which comprises:
  (a) cooling said vapor phase oxidation product to a temperature of about 130° C. or greater; and
  (b) delivering said vapor phase oxidation product to a contacting means which is capable of causing said vapor phase oxidation product to come into contact with at least one by-product stream having a freezing point which is lower than the freezing point of pure phthalic anhydride such that a substantial portion of the phthalic anhydride contained within said vapor phase oxidation product transfers from the vapor phase to a liquid phase and a substantial portion of the by-products contained in the by-product stream which are more volatile than phthalic anhydride transfer from the liquid phase to the vapor phase and wherein a vapor-to-liquid weight ratio in the range between about 2 to 20 is exhibited within said contacting means, provided said by-product stream contains benzoic acid in an amount of less than 8 mole %, based on the total concentration of said by-product stream, thereby forming a liquid phase phthalic anhydride product having a phthalic anhydride concentration in the range between about 50 to 100 wt. %, and a first vapor stream; said contacting means is also capable of separating said liquid phase phthalic anhydride product from said first vapor stream.

6. The process according to claim 5 wherein said liquid phase phthalic anhydride product concentration is in the range between about 90–100 wt. %.

7. The process according to claim 6 wherein said liquid phase phthalic anhydride product concentration is in the range between about 95 to 99.8 wt. %.

8. The process according to claim 5 wherein said contacting means is selected from the group consisting of: a low pressure drop counter-current gas/liquid contactor, a rectification tower, a flash tower and a wetting tower.

9. The process according to claim 8 wherein said low pressure drop counter-current gas/liquid contactor comprises between about 2 to 10 equilibrium stages.

10. The process according to claim 5 wherein said benzoic acid is present in said by-product stream in an amount between about 1–6 mole %.

11. The process according to claim 5 further comprising the steps of:
  (c) removing said liquid phase phthalic anhydride product from said contacting means as bottoms;
  (d) removing said first vapor stream from said contacting means as overhead;
  (e) cooling said first vapor stream to a temperature in the range between about 25° C. to 80° C., thereby forming a first by-product stream and a second vapor stream;
  (f) separating said first by-product stream from said second vapor stream; and
  (g) recycling at least a portion of said first by-product stream to the upper section of said contacting means.

12. The process according to claim 11 further comprising the step of separating said liquid phase phthalic anhydride product into a crude phthalic anhydride stream and a second by-product stream.

13. The process according to claim 12 further comprising the steps of cooling said second by-product stream to a temperature in the range between about 40° C. to 120° C.;

and recycling at least a portion of said second by-product stream to said contacting means.

14. The process according to claim 11 further comprising the step of recycling between about 0 to 50 wt. % of said liquid phase phthalic anhydride product of step (c) to said contacting means, whereby said liquid phase phthalic anhydride product is only used for temperature and composition control.

15. The process according to claim 5 further comprising the following steps:

(c) cooling said first vapor stream to a temperature in the range between about 25° C. to 80° C. in the upper section of said contacting means, thereby forming a first by-product stream and a second vapor stream;

(d) separating said first by-product stream from said second vapor stream in said upper section;

(e) transferring the first by-product stream to the top of said contacting means;

(f) removing said liquid phase phthalic anhydride product from said contacting means as bottoms; and (g) removing said second vapor stream from said contacting means as overhead.

16. The process according to claim 5 wherein said vapor phase oxidation product in step (a) is cooled to a temperature in the range between about 130° C. to 177° C.

17. The process according to claim 11 further comprises mixing said second vapor phase stream with an absorbent, thereby forming a maleic anhydride/absorbent stream; and desorbing said maleic anhydride/absorbent stream to form an enriched maleic anhydride stream and a concentrated absorbent stream, recycling at least a portion of said enriched maleic anhydride stream to steps (e), (f) or (g).

18. The process according to claim 5 further comprising the step of:

removing at least a portion of said first by-product stream from said contacting means, wherein said first by-product stream comprises at least one acid selected from the group consisting of: phthalic acid, maleic acid and citraconic acid;

subjecting said first by-product stream which is removed from said contacting means to sufficient temperature and time to convert any of said acids into their respective anhydrides, thereby forming a dehydrated first by-product stream; and recycling said dehydrated first by-product stream containing the converted acids to said contact means.

19. The process according to claim 5 further comprising the step of:

removing at least a portion of said first by-product stream from said contacting means, wherein said first by-product stream comprises at least one acid selected from the group consisting of: phthalic acid, maleic acid and citraconic acid;

flashing said first by-product stream which is removed from said contacting means to convert any of said acids into their respective anhydrides, thereby forming a dehydrated first by-product stream; and recycling said dehydrated first by-product stream containing the converted acids to said contact means.

20. The process according to claim 11 wherein said first by-product stream is recycled to the upper section of said contacting means by pulsing the flow of said first by-product stream.

21. The process according to claim 9 further comprising the steps of:

removing a liquid mixture comprising said by-product stream and said liquid phase phthalic anhydride product from below at least one said equilibrium stage; and recycling said liquid mixture to a top portion of said equilibrium stage; whereby the liquid to vapor ratio is increased.

* * * * *